(12) United States Patent
Schmidt et al.

(10) Patent No.: US 9,095,636 B2
(45) Date of Patent: Aug. 4, 2015

(54) CATALYTIC SUBSTRATES AND METHODS FOR CREATING CATALYTIC COATINGS FOR INDOOR AIR QUALITY APPLICATIONS

(75) Inventors: Wayde R. Schmidt, Pomfret Center, CT (US); Tania Bhatia Kashyap, Middletown, CT (US); Treese Hugener-Campbell, Coventry, CT (US)

(73) Assignee: CARRIER CORPORATION, Farmington, CT (US)

( * ) Notice: Subject to any disclaimer, the term of this patent is extended or adjusted under 35 U.S.C. 154(b) by 1163 days.

(21) Appl. No.: 13/121,517

(22) PCT Filed: Sep. 16, 2009

(86) PCT No.: PCT/US2009/057081
§ 371 (c)(1),
(2), (4) Date: Jun. 2, 2011

(87) PCT Pub. No.: WO2010/036543
PCT Pub. Date: Apr. 1, 2010

(65) Prior Publication Data
US 2011/0224066 A1 Sep. 15, 2011

Related U.S. Application Data

(60) Provisional application No. 61/100,925, filed on Sep. 29, 2008.

(51) Int. Cl.
*B01J 21/04* (2006.01)
*B01J 23/00* (2006.01)
*B01J 23/02* (2006.01)
(Continued)

(52) U.S. Cl.
CPC .............. *A61L 9/205* (2013.01); *B01D 53/885* (2013.01); *B01J 35/004* (2013.01); *B01J 37/0225* (2013.01); *B01J 37/342* (2013.01); *B01J 37/348* (2013.01); *A61L 2209/14* (2013.01); *B01D 2255/802* (2013.01); *B01D 2257/708* (2013.01);
(Continued)

(58) Field of Classification Search
USPC .............. 502/350, 439, 515, 527.16, 527.19, 502/527.24; 428/116
See application file for complete search history.

(56) References Cited

U.S. PATENT DOCUMENTS 5,711,071 A * 1/1998 Fromson et al. ......... 29/890.046
5,753,322 A 5/1998 Yamaguchi et al.
(Continued)

FOREIGN PATENT DOCUMENTS

| JP | 10237362 A | 9/1998 |
|---|---|---|
| JP | 2003154272 A | 5/2003 |
| KR | 20040095581 A | 11/2004 |

OTHER PUBLICATIONS

International Search Report dated May 3, 2010 for PCT/US2009/057081, International Filing Date Sep. 16, 2009.
(Continued)

*Primary Examiner* — Patricia L Hailey
(74) *Attorney, Agent, or Firm* — Cantor Colburn LLP

(57) ABSTRACT

A catalytic device for removal of airborne volatile compounds from air includes a substrate and an electrodeposited catalytic coating. The substrate has a surface. The electrodeposited catalytic coating is on the surface of the substrate. The electrodeposited catalytic coating includes a catalyst that is capable of interacting with airborne volatile compounds. The electrodeposited catalytic coating has a multimodal porosity distribution.

13 Claims, 3 Drawing Sheets

(51) Int. Cl.
*B32B 3/12* (2006.01)
*A61L 9/20* (2006.01)
*B01D 53/88* (2006.01)
*B01J 37/02* (2006.01)
*B01J 37/34* (2006.01)
*B01J 21/06* (2006.01)
*B01J 35/00* (2006.01)
*B01J 35/04* (2006.01)

(52) U.S. Cl.
CPC ............ *B01J 21/063* (2013.01); *B01J 35/0013* (2013.01); *B01J 35/04* (2013.01)

(56) References Cited

U.S. PATENT DOCUMENTS

| | | | |
|---|---|---|---|
| 6,083,871 A * | 7/2000 | Fromson et al. | 502/439 |
| 6,214,765 B1 * | 4/2001 | Fromson et al. | 502/355 |
| 6,479,430 B1 * | 11/2002 | Fromson et al. | 502/439 |
| 8,277,899 B2 * | 10/2012 | Krogman et al. | 427/385.5 |
| 8,344,238 B2 * | 1/2013 | Gronet et al. | 136/243 |
| 2002/0050479 A1 | 5/2002 | Scott | |
| 2003/0050196 A1 * | 3/2003 | Hirano et al. | 507/238 |
| 2004/0258581 A1 | 12/2004 | Wei et al. | |
| 2013/0168228 A1 * | 7/2013 | Ozin et al. | 204/157.9 |

OTHER PUBLICATIONS

Written Opinion dated May 3, 2010 for PCT/US2009/057081, International Filing Date Sep. 16, 2009.

Extended European Search Report for corresponding EP Application No. 09816709.1 dated Jul. 4, 2012, 7 pages.

* cited by examiner

CATALYTIC SUBSTRATES AND METHODS FOR CREATING CATALYTIC COATINGS FOR INDOOR AIR QUALITY APPLICATIONS

CROSS REFERENCE TO RELATED APPLICATIONS

The present application claims the benefit of PCT Application, Serial No. PCT/US2009/057081, filed Sep. 16, 2009 and U.S. Provisional Ser. No. 61/100,925, filed Sep. 29, 2008, the contents each of which are incorporated herein by reference thereto.

BACKGROUND

Some buildings utilize air purification systems to remove airborne substances such as benzene, formaldehyde, and other contaminants from the air supply. Some of these purification systems include photocatalytic reactors that utilize a substrate or cartridge containing a photocatalyst oxide. When placed under an appropriate light source, typically a UV light source, the photocatalyst oxide interacts with airborne water molecules to form hydroxyl radicals or other active species. The hydroxyl radicals then attack the contaminants and initiate an oxidation reaction that converts the contaminants into less harmful compounds, such as water and carbon dioxide. It is further believed that the combination of water vapor, suitably energetic photons, and a photocatalyst also generates an active oxygen agent like hydrogen peroxide as suggested by W. Kubo and T. Tatsuma, 20 Analytical Sciences 591-93 (2004).

A commonly used UV photocatalyst is titanium dioxide ($TiO_2$), otherwise referred to as titania. Degussa P25 titania and tungsten oxide grafted titania catalysts (such as tungsten oxide on P25) have been found to be especially effective at removing organic contaminants under UV light sources. See U.S. Pat. No. 7,255,831 "Tungsten Oxide/Titanium Dioxide Photocatalyst for Improving Indoor Air Quality" by Wei et al.

SUMMARY

A catalytic device for removal of airborne volatile compounds from air includes a substrate and an electrodeposited catalytic coating. The substrate has a surface. The electrodeposited catalytic coating is on the surface of the substrate. The electrodeposited catalytic coating includes a catalyst that is capable of interacting with airborne volatile compounds. The electrodeposited catalytic coating has a multimodal porosity distribution.

DETAILED DESCRIPTION

Figure 1:
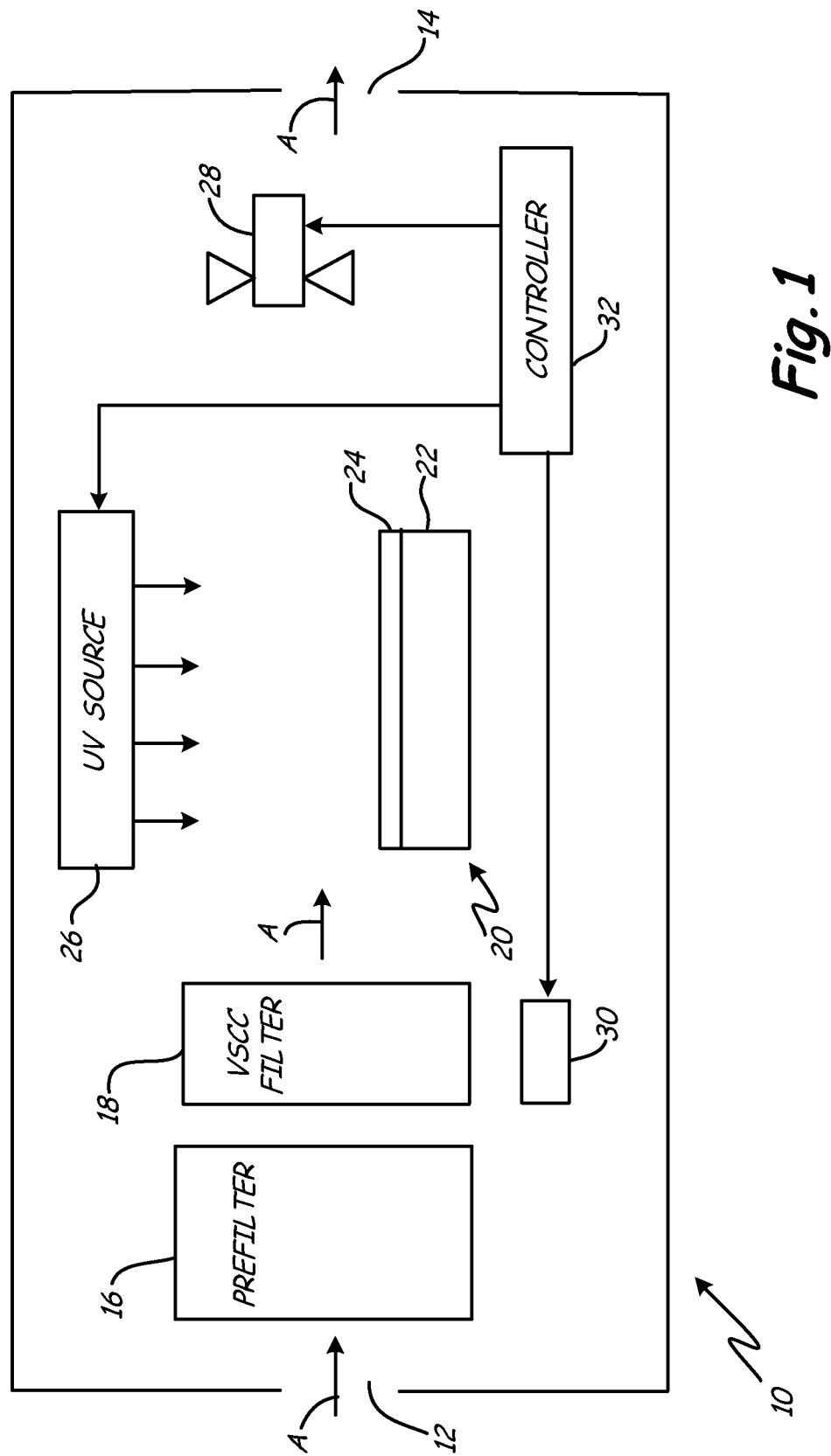
FIG. 1 is a schematic diagram of an ultraviolet photocatalytic oxidation air purification system.

FIG. 1 is a schematic diagram of an ultraviolet photocatalytic oxidation air purification system 10, which includes inlet 12, outlet 14, optional prefilter 16, volatile silicon containing compound (VSCC) filter 18, photocatalytic reactor 20 (which includes substrate 22, catalytic coating 24 and UV source 26) and fan 28. An optional collector 30 may be used to temporarily collect certain volatile compounds such as volatile organic compounds (VOCs) prior to transfer through photocatalytic reactor 20. For example, an adsorbent bed (e.g. activated carbon or zeolites) may be used to collect VOCs for subsequent release (e.g. through heating and subsequent volatilization of the collected VOCs) into photocatalytic reactor 20. Collector 30 may be integrated or incorporated into VSCC filter 18. Controller 32 coordinates the operation of collector 30 with the operation of fan 28 and UV source 26. For example, collector 30 may be operated when UV source 26 is not in operation. In some cases, fan 28 may be operated in conjunction with collector 30; for example, to draw moist or heated air into VSCC filter 18 to further the mineralization process.

Fan 28 draws ambient air into system 10 through inlet 12. Airstream A passes through prefilter 16 and VSCC filter 18, and then through photocatalytic reactor 20 and fan 28 to outlet 14. Prefilter 16 removes dust and particles by trapping the particles and dust. VSCC filter 18 removes volatile silicon containing compounds (VSCCs) so that they do not reach photocatalytic coating 24 and degrade performance of photocatalytic reactor 20. Other volatile organic compounds (VOCs) may also be removed by adsorption on either filter 16 or 18. Although FIG. 1 depicts prefilter 16 and VSCC filter 18 as separate structures, VSCC filter 18 and prefilter 16 may be integrated or incorporated into one filter.

When exposed to UV radiation from UV source 26, catalytic coating 24 containing a photocatalyst on substrate 22 interacts with airborne water molecules to produce reactive species such as hydroxyl radicals, hydrogen peroxide, hydrogen peroxide radicals and superoxide ions. These reactive species interact with VOCs in the air to transform the VOCs into byproducts such as carbon dioxide and water. Therefore, airstream A contains less contaminants as it exits system 10 through outlet 14 than it contained when entering system 10 through inlet 12. Titania is one example of a photocatalyst.

Catalytic coating 24 may also contain a combination of photocatalytic and thermocatalytic particles. Example thermocatalysts include gold, manganese oxide and platinum. Gold acts as an oxidation catalyst to convert carbon monoxide to carbon dioxide in the presence of oxygen. Manganese oxide decomposes ozone to molecular oxygen. Platinum oxidizes low polarity organic compounds to carbon dioxide in the presence of oxygen. In one example, catalytic coating 24 may contain titania and gold particles.

In FIG. 1, substrate 22 is depicted schematically as a flat plate. In practice, substrate 22 can take a number of different forms, which may be configured to maximize surface area on which catalytic coating 24 is located or to maximize the extent of non-laminar (e.g. turbulent) flow through the substrate. Porous substrates may be used such as honeycombs, segmented and radially offset arrays of discrete honeycomb structures, wire meshes, screens, corrugated structures, woven structures, non-woven structures, felts, and fabrics. Substrate 22 may also be a mixture of materials. Substrate 22 can be configured as a flat structure, a singly curved structure or a multicurved structure. Additionally, substrate 22 can be configured as simultaneously both a flat and a curved structure.

Substrate 22 is coated with catalytic coating 24. Previously, the UV photocatalyst coating was typically applied to a substrate (e.g. a honeycomb structure) by spray coating or dip coating. Spray coating results in lost material due to overspraying, and restricts the coating of features out of the line-of-sight of the spray (e.g. undercuts, shadowed areas, deep channels, etc.). For example, spray coating of deep channels within a honeycomb structure would generally result in non-uniform coatings or blocked cell openings. Dip coating is strongly dependent on the orientation of the part to be coated and the relative dipping direction. Spray and dip coating methods result in a non-uniform coating, which is disadvantageous when discrete multilayered coatings are desired.

Electrodeposition techniques use electrical energy and potential gradients to deposit charged catalytic particles or precursors (e.g. ions, polyions, complexes) onto a surface, such as a substrate or a filter. These techniques are non-line-of-sight deposition methods that can coat accessible, but hidden, shadowed, embedded, interior, undercut or not easily visible surfaces, resulting in a uniform coating. Electrodeposition is particularly amenable to the formation of uniform films on surfaces with complicated shapes, impregnation of porous surfaces, and deposition on select areas of surfaces. The use of an applied electric field during electrodeposition techniques may reduce undesired agglomeration of particles during application of the coating. Additionally, electrodeposition techniques may result in improvements to uniformity and reproducibility of the coating and decreased costs of applying the coating.

The photocatalytic or thermocatalytic property of catalytic coating 24 is only one of the attributes of catalytic coating 24. Catalytic coating 24 may also increase the surface area of substrate 22 through its porosity. An increased surface area is typically accompanied by an increase in active sites, thereby increasing the interactive or adsorptive properties of the surface. Electrodeposition of catalytic coating 24 results in catalytic coating 24 having a multimodal porosity distribution. For example, the porosity of catalytic coating 24 may be comprised of the native or inherent porosity of the particles used in the deposition process and the porosity of the coating (coating porosity) which is created by the deposition process. The porosity may be measured by surface area and microscopy. In one example, the particles have pore diameters of about 4 nanometers or greater. In another example, the particles have pore diameters between about 10 nanometers and about 45 nanometers. In a further example, the coating has pore diameters between about 0.5 microns and about 1.5 microns. The pore diameter may be measured by the Barrett, Joyner, Halenda (BJH) adsorption technique that is well known to those skilled in the art and is typically an option on automated surface area determination equipment. The original reference describing the BJH technique is E. P. Barrett, L. G. Joyner, P. P. Halenda, J. Am. Chem. Soc. 73, (1951), 373-80.

Figure 2:
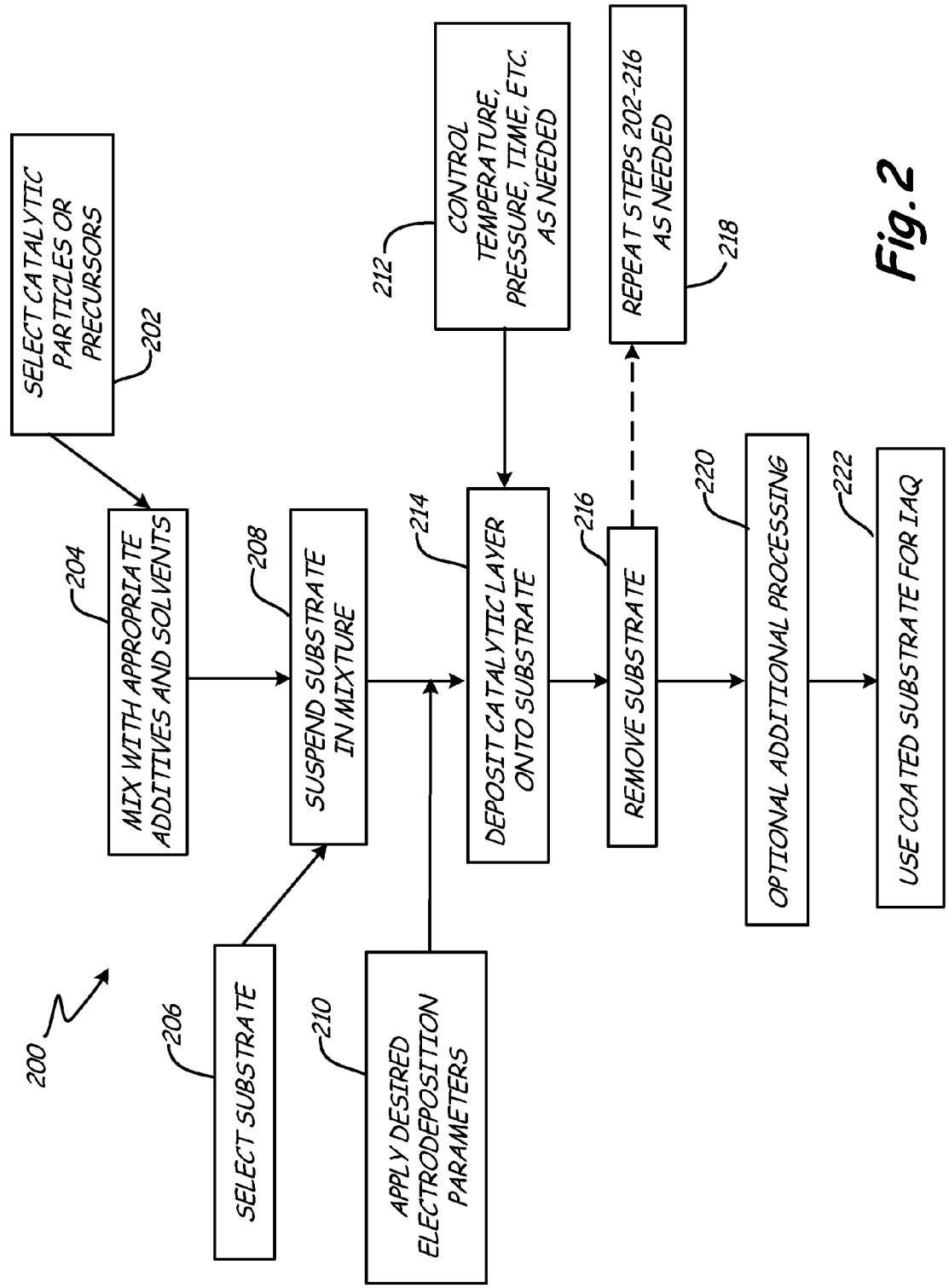
FIG. 2 is a flow diagram of an electrodeposition process.

The flowchart in FIG. 2 illustrates an electrodeposition process. In catalyst electrodeposition 200, catalytic particles or precursors are selected (step 202). Selection of the mixture materials depends on the electrodeposition technique used and the desired characteristics of the electrodeposited layer and coating, as will be further discussed. In one example, the catalytic particles may be nanoparticles having average diameters between about 4 nanometers and about 100 nanometers. In another example, the catalytic particles may have average diameters between about 0.1 micron and about 1 micron. In a further example, the catalytic particles may have average diameters between about 1 micron and about 10 microns. In a further example, the particles may be catalytic or non-catalytic particles or mixtures thereof having average diameters between about 4 nanometers and 10 microns may be used. Agglomerates of catalytic particles are also possible and these may be as large as tens of microns. The catalytic particles may be photocatalytic, thermocatalytic or a mixture thereof. In one example, the catalytic particles are metal oxides. In another example, the catalytic particles include metal oxides in combination with other metal oxides, semiconductors, metals or metal containing compounds such as titanium dioxide (titania), tungsten oxide, manganese dioxide, and gold. Of course it is contemplated that the term 'metal oxide' includes mono, di, trioxide and non-integer stoichiometries as well as oxygen deficient (submono) stoichiometries. The catalytic particles may also contain nanoengineered photocatalysts. The catalytic particles may be processed specially prior to use to render them more suitable for forming a mixture. For example, particles of titanium dioxide may be ground and sieved to create a specific particle size and particle size distribution profile. In another example, nanometer sized particles of titanium dioxide may be functionalized with organic moieties such as carbonyl groups (e.g. carboxylic acid) or nitrogen functionalities (e.g. amines) to afford particular interaction with additives and/or solvents.

The catalytic precursor may be any material that can transform into catalytic particles. One example of the catalyst precursor is titanium tetrachloride. Catalytic precursors are selected based on their solubility in the desired solvent as well as the targeted catalyst composition. A mixture of precursors and catalytic particles is also contemplated.

After the catalytic particles or precursors are selected, they are mixed with appropriate additives and solvents to create a mixture, such as a slurry or a solution (step 204). In one example, the mixture is a slurry containing a dispersion of catalytic particles. In another example, the mixture is a solution containing dissolved catalytic particles and/or catalytic precursors. In a further example, the mixture contains dispersed catalytic particulates and dissolved precursors.

If catalytic particles are used, an appropriate amount of catalytic particles are mixed with the additives and solvents. In one example, the volume percentage of catalytic particles in the mixture is at least about 5%. In another example, the volume percentage of catalytic particles in the mixture is at least about 10%. In another example, the catalyst particles are present in a concentration of between 0.1 to 10 grams of particles (or powder) per 1 milliliter of dispersing media/solvent. In contrast, in a colloidal suspension the volume percentage of particles is less than 4% and the weight loading is 20% or less.

Similarly, an appropriate amount of precursor is mixed with the additives and solvent. In one example, the concentration of the dissolved catalytic precursor in the mixture is at least about 0.001 M. In another example, the concentration of the dissolved catalytic precursor in the mixture is at least about 0.01 M.

In a separate step, the substrate is selected (step 206). Any electrically conducting structure or non-electrically conducting structure coated with a conductive coating may be a substrate. Example substrate materials include pure metals and alloys, plastics, glass, ceramics, carbon and composites. The structure may be inherently electrically conductive (e.g. metals and carbon), incorporate conductive fillers to render it electrically conductive (e.g. filled plastics) or may be coated or otherwise modified to render it electrically conductive (e.g. continuous metal coating on a plastic or glass substrate). Substrate structures include, but are not limited to sheetstock, photoetched foils, expanded slit sheets, meshes, fibrous webs, braided structures, nonwoven or woven structures, open cell foam structures and composites. Additional porous substrate examples include honeycombs, segmented and radially offset arrays of discrete honeycomb structures, screens, corrugated structures, fabrics and felts such as carbon felts. Other fiber based metallic and non-metallic structures are also contemplated as suitable substrates.

Additionally, an electric field or potential gradient can pull particles or precursors through an otherwise non-conductive porous structure towards a more electrically conductive structure in order to build a catalyst layer on the non-conductive structure. Therefore, a non-conducting porous structure can be a substrate. For example, if a non-conductive plastic screen is desired as a substrate, the screen is placed adjacent a conducting surface. When an electric field is applied to the conducting surface, the particles in the mixture are drawn towards the conducting surface and pass through the non-conducting screen. Eventually, the particles build up and create a coating on the screen. In another example, a porous coating on a conducting substrate can be modified by applying an electric field sufficient to pull particles or precursors in a mixture into the pores of the porous coating as they move towards the conducting substrate. In this manner, a multimaterial composite coating can be fabricated.

The substrate may be selectively masked to prevent or enhance particular deposited layers. In one example, one portion or section of a substrate is masked to prevent deposition of the catalytic particles onto the masked portion. When used in an indoor air quality (IAQ) application, the masked portion functions as a prefilter while the unmasked portion, on which catalytic particles were deposited, functions as a catalytic substrate. In another example where a later bonding process requires bare metal, the edges of a metal substrate, such as a disk, are masked to prevent deposition on the edges. After electrodeposition, the bare metal edges can be bonded to a system assembly. In another example, a downstream portion of a substrate is masked. In an IAQ application, the substrate's masked portion may be used to promote air flow and manage pressure drop because of the lack of a catalytic coating.

After selection, the substrate is suspended in the mixture (step 208). The substrate, having a charge opposite that of the catalytic particles, acts as an electrode. A counter electrode is added to complete the circuit. The desired electrodeposition parameters are applied to the mixture (step 210), parameters such as temperature, pressure, and time are controlled as needed (step 212), and a catalytic layer containing catalytic particles is deposited on the substrate (step 214).

Characteristics of the deposited layer, such as thickness and texture, are affected by the substrate material(s), the mixture materials and the processing parameters. The characteristics are also affected by the length of exposure to and magnitude of the potential bias between the electrodes. Additionally, deposition time and the magnitude of current flow within the electrical circuit influence the characteristics of the deposited layer. The application of potential (voltage) bias and current flow or current density can be controlled to improve coating quality and can be generally continuous or intermittent, such as via pulsing or cycling depositions. For example, the current and the catalytic particle composition may be changed so that a textured surface is created on a substrate. The textured surface increases the surface area of the substrate due to its porosity, creating a more adsorbent surface that is desirable for certain IAQ applications.

After the catalytic layer is deposited onto the substrate, the coated substrate is removed from the mixture (step 216). When catalytic particles are deposited, the deposited layer is a catalytic layer and may be capable of interacting with VOCs immediately after deposition. No additional processing is necessary to create catalytic properties in the catalytic layer.

Additional processing may be necessary if a catalytic precursor was used. A catalytic precursor may be transformed into catalytic particles at any point during method 200. For example, the catalytic precursor may form an oxide species upon the application of heat or electric potential. If the catalytic precursor transforms into catalytic particles before or during the electrodeposition, the deposited layer is a catalytic layer and no additional processing is necessary. If the catalytic precursor did not transform into catalytic particles before or during the electrodeposition, additional processing is necessary to create catalytic properties in the layer. In one example, the precursor transforms into catalytic particles when electric potential is applied to the mixture in step 210.

The substrate may be coated one or more times using electrodeposition. Any combination of steps 202-216 may be repeated to deposit one or more additional layers on the substrate (step 218). To form a catalytic coating, at least one layer deposited onto the substrate must be a catalytic layer or a layer having catalytic properties. Additional electrodepositions may also be performed to further tailor the performance properties of the catalytic coating. The additional electrodepositions may use the same or different electrodeposition technique and may result in layers with different compositions, thicknesses, and microstructures. For example, a substrate may be subjected to a series of electrophoretic depositions wherein each deposition uses a mixture having a different composition. In a specific example, a thin layer of manganese oxide thermal catalyst is coated on a substrate and a thicker layer of titanium dioxide photocatalyst is coated onto the manganese oxide coating.

In another example, a first electrodeposited layer may form a base for a second electrodeposited layer. For example, the first electrodeposited mixture may contain larger diameter particles than the second electrodeposited mixture. In a specific example, the first electrodeposited mixture may contain particles having diameters between about 50 nanometers to about 10 microns and the second electrodeposited mixture may contain particles having diameters between about 5 nanometers and about 50 nanometers. In this example, the first layer may contain catalytic or non-catalytic particles, and the second layer may contain catalytic particles so that the catalytic coating has catalytic properties.

The total thickness of the catalytic coating should be considered when depositing the layers. For example, for light activation systems using a photocatalyst, UV light must illuminate the photocatalyst in order for the photocatalyst coating to transform the VOCs into relatively harmless byproducts. If the coating is too thick, the light cannot illuminate the innermost layers and the coating is ineffective. In a specific example, the total thickness of a catalytic coating on a substrate is between about 1 micrometer and about 50 micrometers so that a UV light source can illuminate the innermost layers of the catalytic coating.

After the final layer is deposited, the substrate can be subjected to additional processing such as a chemical reaction, exposure to alternate atmosphere compositions or reduced pressures, thermal treatment or exposure to radiation to change or introduce alternative properties of the catalytic layer (step 220). In one example, liquid remaining from the electrodeposition process is removed from the catalytic coating using reduced pressure at room temperature or by heating the catalyst support. In another example, the catalytic coating is densified or strengthened by heating the substrate. In another example, the phase of the catalytic coating is converted into a more desired phase, composition or microstructure by heating the substrate and coating (e.g. crystallization of the catalytic coating). When complete, the coated substrate is used for an IAQ application (Step 222).

Figure 3:
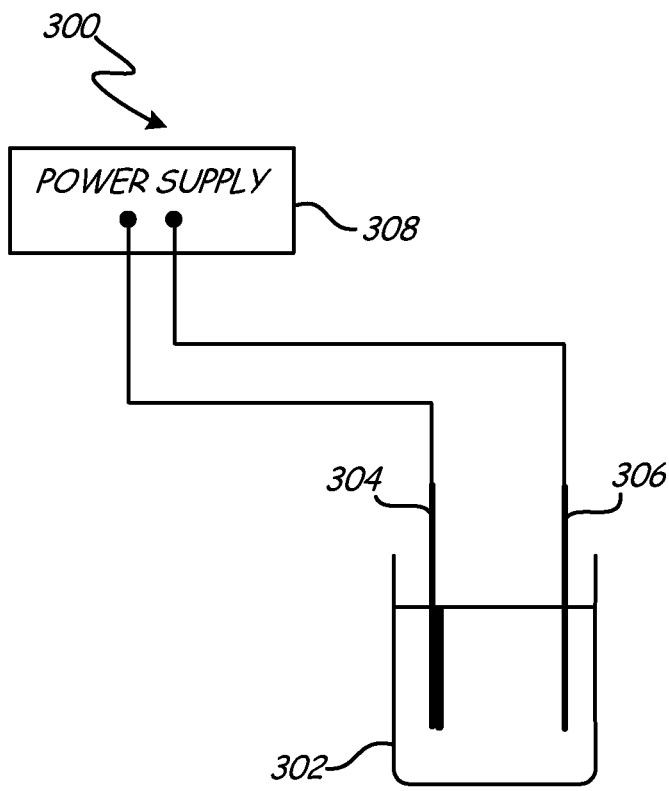
FIG. 3 is a schematic diagram of an electrophoretic deposition system.

Two electrodeposition techniques that can be used to form a catalytic coating are electrophoretic deposition (EPD) and electrolytic deposition (ELD). EPD is used to create relatively thick film coatings and to laminate structures onto dense or porous supports. FIG. 3 illustrates an EPD system. EPD system 300 includes slurry 302, substrate electrode 304, electrode 306, and power supply 308. In one example, slurry 302 contains a dispersion of catalytic particulates. Slurry 302 is created by mixing particles, generally in powder form, with additive(s) and a dispersing media. As described previously the particles may be catalytic or non-catalytic particles, as long as at least one electrodeposited layer contains catalytic particles so that a catalytic coating is formed. The catalytic particles may be photocatalytic, thermocatalytic or a mixture thereof. Example catalytic particles include a metal oxide, alone or in combination with other metal oxides, semiconductors, metals or metal containing compounds such as titanium dioxide (titania), tungsten oxide, manganese dioxide, and gold. Of course it is contemplated that the term 'metal oxide' includes mono, di, trioxide and non-integer stoichiometries as well as oxygen deficient (submono) stoichiometries.

The catalytic particles may be nanoparticles or nanoengineered photocatalysts having average diameters between about 4 nanometers and about 100 nanometers. In another example, the catalytic particles may have average diameters between about 0.1 micron and about 1 micron. In a further example, the catalytic particles may have average diameters between about 1 micron and about 10 microns. In a further example, the particles may be catalytic or non-catalytic particles or a mixture thereof having an average diameter between about 4 nanometers and 10 microns may be used. Agglomerates of catalytic particles are also possible and these may be as large as tens of microns. A mixture of precursors and particulates is also contemplated. The catalytic particles may be processed specially prior to use to render them more suitable for slurry formation. For example, particles of titanium dioxide may be ground and sieved to create a specific particle size and particle size distribution profile. In another example, particles may be selectively functionalized to stabilize them further in the presence of desired additives.

Example additives include binders, dispersing agents, and pH modifiers (e.g. acids and bases). The dispersing media can be any liquid that aids creation of a uniform dispersion of the particles in slurry 302, such as surfactants, alcohols, polyelectrolytes, solutions or water. The dispersing media must have sufficiently low conductivity and may be an organic solvent or blend of solvents.

The catalytic particles, additive(s) and dispersing media are mixed to form slurry 302. In one example, the volume percentage of catalytic particles in slurry 302 is at least about 5%. In another example, the volume percentage of catalytic particles in slurry 302 is at least about 10%. In another example, the catalyst particles are present in a concentration of between 0.1 to 10 grams of powder per 1 milliliter of dispersion media/solvent. In contrast, a colloidal suspension has less than 4% by volume particles and 20% or less by weight particle loading.

Substrate electrode 304 and electrode 306 are submerged in slurry 302. Substrate electrode 304 contains a substrate on which the catalytic coating will be deposited. The substrate must have a charge predominantly opposite that of the catalytic particles during deposition. Power supply 308 supplies electrical energy to slurry 302. The electrical energy provides a bias that attracts the catalytic particles to the surface of the substrate where the catalytic particles are deposited to form a catalytic layer. EPD produces a deposition rate of approximately 1 to $10^3$ micrometers per minute and a deposit thickness of approximately 1 to $10^3$ micrometers. Uniformity of the deposited layer is limited by the size of particles used and is controlled by the electrodeposition parameters, including the electric field. The processing conditions of system 300 can be varied to control the microstructure of the deposited layer. For example, the deposit thickness is controlled by varying the deposition time, voltage, and current density, and the deposit stoichiometry is controlled by the temperature at which the deposition occurs and the stoichiometry of the particles (or powder) used for the deposition. Although described with reference to catalytic particles, EPD system 300 may be used with non-catalytic particles.

When catalytic particles are used, the deposited layer is a catalytic layer having catalytic properties. A substrate containing electrodeposited catalytic particles may immediately be used in an IAQ application. No additional processing is necessary to create catalytic properties in the deposited layer.

In a specific example, 100 grams of titania powder is mixed with 1 liter of liquid dispersing media ethyl alcohol, 2.2 grams of additive polyvinyl butyral and 2.5 grams of additive phosphate ester to create slurry 302. A pH modifier is added to raise the pH of slurry 302 above the isoelectric point of titania. Slurry 302 is maintained at approximately 20 degrees Celsius. Substrate 304, which has a positive charge, is lowered into slurry 302 and a current density of 0.1 milliamps per cm2 is applied. A thick, fairly uniform and smooth layer is deposited on substrate 304.

Figure 4:
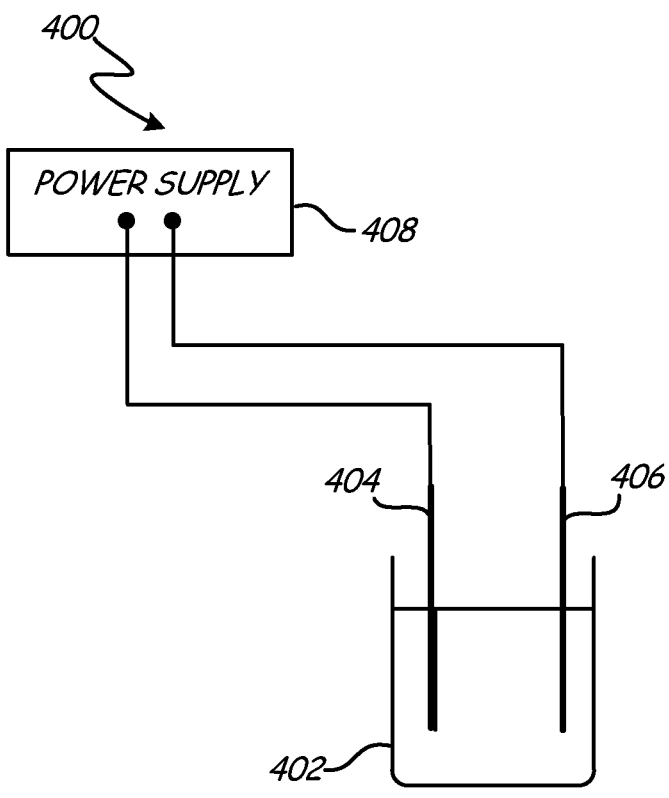
FIG. 4 is a schematic diagram of an electrolytic deposition system.

Electrolytic deposition (ELD) is another electrodeposition technique that can be used to deposit a catalytic layer. ELD creates relatively thin film coatings on substrates. FIG. 4 illustrates an ELD system. ELD system 400 includes solution 402, substrate electrode 404, electrode 406, and power supply 408. Solution 402 is created by dissolving catalytic particles or a precursor that can transform to catalytic particles into a solvent or liquid dispersing media. Example catalytic particles include a metal oxide, alone or in combination with other metal oxides, semiconductors, metals or metal containing compounds such as titanium dioxide (titania), tungsten oxide, manganese dioxide, and gold. Of course it is contemplated that the term 'metal oxide' includes mono, di, trioxide and non-integer stoichiometries as well as oxygen deficient (submono) stoichiometries.

The catalytic particles may be nanoparticles or nanoengineered photocatalysts having average diameters between about 4 nanometers and about 100 nanometers. In another example, the catalytic particles may have average diameters between about 0.1 micron and about 1 micron. In a further example, the catalytic particles may have average diameters between about 1 micron and about 10 microns. In a further example, the particles may be either catalytic or non-catalytic particles or a mixture thereof having an average diameter between about 4 nanometers and 10 microns may be used. Agglomerates of catalytic particles are also possible and these may be as large as tens of microns.

A catalytic precursor is any material that can transform into catalytic particles. When precursors to catalytic materials are used, they are selected based on their solubility in the desired solvent as well as the targeted catalyst composition. Suitable precursors include metal organic or organometallic species, metal alkoxides, metal halides, metal oxo compounds and mixtures thereof. A mixture of precursors and particulates is also contemplated.

The solvent or liquid dispersing media must have a sufficiently high conductivity, and can be a mixed solvent, such as a mixture of water and an organic solvent. Additives such as binders, surfactants, ionic species, acids, bases and polyelectrolytes can be used to increase the stability of the solution used in the ELD process.

Catalytic particles or a precursor that can transform into catalytic particles are dissolved into a solvent or liquid dispersing media to create solution 402. In one example the concentration of dissolved precursor is at least about 0.001 M. In another example, the concentration of dissolved precursor is at least about 0.01 M. In another example, the volume percentage of catalytic particles in solution 402 is at least about 5%. In another example, the volume percentage of catalytic particles in solution 402 is at least about 10%. In contrast, a colloidal suspension has less than 4% by volume particles and 20% or less by weight particle loading.

Substrate electrode 404 and electrode 406 are submerged in solution 402. Substrate electrode 404 contains a catalyst support on which the catalytic coating will be deposited. The substrate must have a charge predominantly opposite that of the catalytic particles during deposition. Power supply 408 supplies electrical energy to solution 402. The electrical energy provides a bias that attracts catalytic particles in the form of ions or complexes to the surface of the substrate where the catalytic particles are deposited to form a catalytic layer. In ELD system 400, reactions occur at electrodes 404 and 406; e.g. there is electrochemical generation of OH— species and neutralization of the cationic species in the solution. ELD produces a coating deposition rate of approximately $10^{-3}$ to 1 micrometer(s) per minute and a deposit thickness of approximately $10^{-3}$ to 10 micrometers. Uniformity of the deposited layer is generally on a nanometer or sub-nanometer scale. The processing conditions of system 400 may be varied to control the microstructure of the deposited coating. For example, the deposit thickness is controlled by varying the deposition time, voltage and current density, and the deposit stoichiometry is controlled by the temperature at which the deposition occurs and the selective use of precursor chemistry(ies). Although ELD system 400 has been described with reference to catalytic precursors and particles, non-catalytic precursors and particles may be used.

The precursor may be transformed into catalytic particles before, during or after the deposition. For example, a precursor may transform into catalytic particles when a processing condition, such as heat or voltage, is applied to precursor. If the transformation occurs before or during the deposition, the deposited layer is a catalytic layer having catalytic properties. No additional processing is necessary for the substrate to be used in an IAQ system. If the transformation did not occur before or during the deposition, additional processing is necessary to create a catalytic properties in the deposited layer.

In a specific example, 5 millimolar TiCl4 precursor is dissolved in a dispersion media comprised of a 3:1 by volume methyl alcohol and water mixture. This media also contains 0.1M $H_2O_2$ additive. A substrate is submerged in the solution and a current density of 20 milliamps per $cm^2$ is applied to the solution at approximately 1 degree Celsius. The electrical energy oxidizes the titanium tetrachloride, and a titanium dioxide layer is formed on the substrate.

Electrodeposition of the catalytic coating has several advantages compared to the prior catalytic coating methods of spray or dip coating. For example, electrodeposition techniques are low cost, require simple equipment, are non-line-of-sight and are easy to scale up. Electrodeposition also has options for processing at low temperatures, and the coating deposition rate is highly controllable and generally high; up to tens of $mg/cm^2$ per minute for EPD and ones of $mg/cm^2$ per minute for ELD.

Electrodeposition conserves the catalytic coating materials and reduces waste. In electrodeposition, catalytic particles that do not adhere to the surface can be used in a subsequent deposition process. In contrast, spray coating wastes significant amounts of particle-containing spray in overspray.

Electrodeposition produces a coating that is more uniform and reproducible. For example, spray or dip coating a honeycomb structure can result in the coating blocking or covering some cells. However, in electrodeposition, the coating particles or precursors are attracted to the honeycomb's surface, including those surfaces outside the direct line-of-sight, by electrical energy. No cells are blocked or covered. In another example, open cell, electrically conductive foam structures can be evenly coated using electrodeposition. Further, electrodeposition results in a more uniform coating because it is based on the three-dimensional structure of the substrate through which current must flow and is a non-line-of-sight deposition method. Electrical energy creates a bias which directs the coating particles to all the surfaces of the substrate, even hidden surfaces. In comparison, spray coating is a line-of-sight method and only coats visible surfaces (i.e. those directly inline with incoming light). For example, electrodeposition would uniformly coat individual fibers deep within a three-dimensional metallic fiber felt that were exposed to the deposition mixture (i.e. solution or slurry), while spray coating would fail to uniformly coat interior fibers within the structure.

Electrodeposition processing conditions, such as deposition time, temperature, applied potential (voltage), and current density, are used to control the thickness of the catalytic layer deposited. This allows electrodeposition techniques to produce more reproducible coatings.

The electrodeposition processing conditions can be varied to carefully control the microstructure, phase(s) (including porosity) and crystallinity of the deposited coating. For example, the porosity of the deposited coating can be controlled through the processing conditions. The porosity of the deposited coating together with the porosity of the deposited particles creates a coating having a multimodal porosity distribution. As explained above, the porosity increases surface area. An increased surface area usually is also accompanied by an increase in active sites, thereby increasing the interactive or adsorptive properties of the surface, which are desirable properties in IAQ applications.

The mechanical stability of electrodeposited coatings prevents blow-off during use. Blow-off occurs when the coating is not secured to the substrate and is blown off by air flow during use. Blow-off decreases the effectiveness of the substrate, especially a catalytic substrate used for indoor air quality applications. Blow-off may also damage equipment downstream. Electrodeposition, especially electrolytic deposition, results in better adhesion of the coating to the substrate and reduces blow-off.

Although the present invention has been described with reference to preferred embodiments, workers skilled in the art will recognize that changes may be made in form and detail without departing from the spirit and scope of the invention.

The invention claimed is:

1. A catalytic device for removal of airborne volatile compounds from air, the catalytic device comprising:
   a substrate having a surface; and
   an electrodeposited coating on the surface, the electrodeposited coating including particles of a catalyst or precursor of a catalyst capable of interacting with airborne volatile compounds, or a mixture of a catalyst and a precursor of a catalyst capable of interacting with airborne volatile compounds, and the electrodeposited coating having a multimodal porosity distribution that includes a native particle porosity and a coating porosity, wherein the particles have pore diameters greater than about 4 nanometers.

2. The catalytic device of claim 1, wherein the particles have pore diameters between about 10 nanometers and about 45 nanometers.

3. The catalytic device of claim 1, wherein the coating has pore diameters between about 0.5 micron and about 1.5 microns.

4. The catalytic device of claim 1, wherein the substrate comprises at least one material selected from a group consisting of: plastics, glass, ceramics, carbon and composites.

5. The catalytic device of claim 1, wherein the electro deposited coating comprises a precursor of a catalyst capable of interacting with airborne volatile compounds or a mixture of a catalyst and a precursor of a catalyst capable of interacting with airborne volatile compounds.

6. The catalytic device of claim 1, wherein the electrodeposited catalytic coating comprises a mixture of at least one photocatalysts and at least one thermal catalyst, or precursors thereof.

7. The catalytic device of claim 1, wherein the electrodeposited catalytic coating is about 1 micron to about 50 micrometers thick.

8. The catalytic device of claim 1, wherein the surface is a metal honeycomb and the catalytic coating includes titanium dioxide.

9. A method of forming a catalytic device for removal of airborne volatile compounds from air, the method comprising:

forming a mixture;

positioning a substrate in the mixture;

electrodepositing particles from the mixture onto the substrate; and creating a catalytic coating on the substrate, wherein the catalytic coating comprises particles of a catalyst or a precursor of a catalyst that is capable of interacting with airborne volatile compounds, or a mixture of a catalyst and a precursor of a catalyst that is capable of interacting with airborne volatile compounds, wherein the electrodeposited coating has a multimodal porosity distribution that includes a native particle porosity and a coating porosity, and the particles have pore diameters greater than about 4 nanometers.

10. The method of claim 9, and further comprising:

forming catalytic particles from a precursor.

11. The method of claim 10, and further comprising:

processing the substrate to change a catalyst property.

12. The method of claim 9, wherein the substrate is an electrically non-conductive porous structure, and the method further comprises applying an electric field or potential gradient through the substrate to pull the nanoparticles towards a more electrically conductive structure, thereby depositing the nanoparticles onto the substrate.

13. The method of claim 9, including the step of electrophoretically depositing a slurry of particles onto the substrate.

* * * * *